(12) United States Patent
Kamm et al.

(10) Patent No.: US 8,906,903 B2
(45) Date of Patent: *Dec. 9, 2014

(54) TOPICAL PHARMACEUTICAL COMPOSITION COMPRISING A CHOLINERGIC AGENT OR A CALCIUM CHANNEL BLOCKER

(71) Applicants: Michael A. Kamm, London (GB); Robin K. S. Phillps, Northwood (GB)

(72) Inventors: Michael A. Kamm, London (GB); Robin K. S. Phillps, Northwood (GB)

(73) Assignee: S.L.A. Pharma AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/685,023

(22) Filed: Nov. 26, 2012

(65) Prior Publication Data
US 2013/0079332 A1 Mar. 28, 2013

Related U.S. Application Data

(63) Continuation of application No. 13/178,567, filed on Jul. 8, 2011, now Pat. No. 8,318,721, which is a continuation of application No. 09/355,928, filed as application No. PCT/GB98/00575 on Feb. 23, 1998, now Pat. No. 8,048,875.

(51) Int. Cl.
| | | |
|---|---|---|
| *A61K 31/554* | (2006.01) | |
| *A61K 31/573* | (2006.01) | |
| *A61K 31/55* | (2006.01) | |
| *A61K 9/00* | (2006.01) | |
| *A61K 31/27* | (2006.01) | |
| *A61K 47/14* | (2006.01) | |
| *A61K 47/10* | (2006.01) | |
| *A61K 47/20* | (2006.01) | |

(52) U.S. Cl.
CPC .............. *A61K 31/554* (2013.01); *A61K 47/14* (2013.01); *A61K 47/10* (2013.01); *A61K 31/573* (2013.01); *A61K 31/55* (2013.01); *A61K 9/0031* (2013.01); *A61K 31/27* (2013.01); *A61K 47/20* (2013.01)
USPC .................................................. 514/211.07

(58) Field of Classification Search
CPC ..................................................... A61K 31/554
USPC .................................................... 514/211.07
See application file for complete search history.

(56) References Cited

U.S. PATENT DOCUMENTS

| | | | |
|---|---|---|---|
| 4,931,279 A | 6/1990 | Bawa et al. | |
| 5,084,281 A | 1/1992 | Dillon | |
| 5,162,315 A | 11/1992 | Rajadhyaksha et al. | |
| 5,288,505 A | 2/1994 | Deboeck et al. | |
| 5,504,117 A | 4/1996 | Gorfire | |
| 5,519,061 A | 5/1996 | Youdim et al. | |
| 5,534,520 A | 7/1996 | Fisher et al. | |
| 5,741,822 A * | 4/1998 | Yesair ........................... 514/734 | |

FOREIGN PATENT DOCUMENTS

| | | |
|---|---|---|
| BE | 1003002 | 10/1991 |
| EP | 0275054 | 7/1988 |
| EP | 0301392 | 2/1989 |
| FR | 2074627 | 1/1970 |
| JP | 07145061 | 6/1995 |
| WO | 95/06466 | 3/1995 |
| WO | 95/32715 | 12/1995 |

OTHER PUBLICATIONS

Carapeti et al., Gut 1999; 45:719-722.
Griffin et al., Colorectal Disease, 4, 430-435 (2002).
Knight et al., British Journal of Surgery 2001, 88, 553-556.
Chrysos et al., "Effect of Nifedipine on tectoanal Motility", Diseases of the Colon and Rectum, vol. 39, No. 2, Feb. 1996, pp. 212-216.
Lund et al., "Aetiology and Treatment of Anal Fissure", British Journal of Surgery, 1996, vol. 83, pp. 1335-1344.
Martindale The Extra Pharmacopoeia, 31$^{st}$ Edition, 1996, pp. 1516-1518, 857-859, 1417-1418.
Loder et al., "Reversible Chemical Sophincterotomy by Local Application of Glyceryl Trinitrate", British Journal of Surgery, 1994, vol. 81, pp. 1386-1389.
Watson et al., "Topical Glyceryl Trinitrate in the Treatment of Chronic Anal Fissure" British Journal of Surgery, 1996, vol. 83, pp. 771-775.
Gorfine, "Treatment of Benign Anal Disease with Topical Nitroglycerin", Disease of the Colon & Rectum, May 1995, vol. 38, pp. 453-457.
Gorfine, "Topical Nitroglycerin therapy for Anal Fissures and Ulcers", The New England Journal of Medicine, Oct. 26, 1995, pp. 1156-1157.
Lund et al., "Use of Glycerly Trinitrate Ointment in the Treatment of Anal Fissure", British Journal of Surgery, 1996, vol. 83, pp. 776-777.
Pitt, "The Effect of Alpha Adrenoceptor Blockade on the Anal Canal in Patients with Chronic and Fissure", Nov. 27, 1996, Abstract.
Loder et al., "Haemorrhoids: Pathology, Pathophysiology and Aetiology", British Journal of Surgery, 1994, vol. 81, pp. 946-954.
Boquet et al., "Diltiazem for Proctalgia Fugax", The Lancet, Jun. 28, 1986, pp. 1493.

(Continued)

*Primary Examiner* — Maria Leavitt
*Assistant Examiner* — Amy M Bunker
(74) *Attorney, Agent, or Firm* — Marianne Fuierer; Moore & Van Allen, PLLC

(57) ABSTRACT

A method and composition are provided for the treatment of an anorectal disorder and for controlling the pain associated therewith. The method comprises administering to a subject in need of such treatment therapeutically effective amounts of a calcium channel blocker either alone or together with a nitric oxide donor. Amlodipine, anipamil, barnidipine, benidipine, bepridil, darodipine, diltiazem, efonidipine, felodipine, isradipine, lacidipine, lercanidipine, lidoflazine, manidipine, mepirodipine, nicardipine, nifedipine, niludipine, nilvadipine, nimodipine, nisoldipine, nitrendipine, perhexiline, tiapamil, verapamil and pharmaceutically acceptable salts thereof, are suitable calcium channel blockers.

2 Claims, 3 Drawing Sheets

(56) References Cited

OTHER PUBLICATIONS

Jonard et al., "Diltiazem and Internal Anal Sphincter", The Lancet, Mar. 28, 1987, pp. 754.

Burleigh et al., Gastroenterology, Sep. 1979, vol. 77, No. 3, pp. 484-490, at p. 484, Abstract.

Sun et al., "Effect of Oral Nicardipine on Anorectoal Function in Normal Human Volunteers and Patients with Irritable Bowl Syndrome", Digestive Diseases and Sciences, 1990, vol. 35, (7) pp. 885-890.

Celik et al., "Hereditary Proctalgia Fugax and Constipation: Report of a Second Family", Gut, 1995, vol. 36, pp. 581-584.

* cited by examiner

TOPICAL PHARMACEUTICAL COMPOSITION COMPRISING A CHOLINERGIC AGENT OR A CALCIUM CHANNEL BLOCKER

CROSS REFERENCE TO RELATED APPLICATIONS

This application is a continuation application claiming priority to U.S. patent application Ser. No. 13/178,567, filed on Jul. 8, 2011, now U.S. Pat. No. 8,318,721, which in turn claimed priority to U.S. patent application Ser. No. 09/355,928 with a filing date of Sep. 13, 1999, now U.S. Pat. No. 8,048,875, which in turn was a 371 application claiming priority to PCT International Application No. PCT/GB98/00575 filed on Feb. 23, 1998.

BACKGROUND OF THE INVENTION

1. Technical Field

This invention relates to the use of a calcium channel blocker or a cholinegic agent, particularly diltiazem and bethanechol, alone and in combination for the treatment of benign anal diseases where there is an associated anal sphincter spasm. The invention particularly relates to the treatment of anal fissures and painful haemorrhoidal conditions.

2. Related Art

A fissure is a split in the skin of the distal anal canal. It is a common complaint in young adults with a roughly equal incidence in both sexes. Acute fissures are very common and most heal spontaneously, but a proportion progress to form a chronic linear ulcer in the anal canal and show great reluctance to heal without intervention.

Treatment has remained largely unchanged for over 150 years and the pathogenesis of anal fissure is not fully understood. The passage of a hard stool bolus has traditionally been thought to cause anal fissure. Thus for acute fissures the avoidance of constipation, such as involving a high bran diet, has been used as treatment for many years.

Anal dilators have also been involved in treatment. Typically a dilator of medium size was coated with anaesthetic jelly and inserted into the anal canal before the passage of stool to prevent exacerbation of the symptoms during defecation. The procedure was inconvenient and success rate was low. The most common treatment, for chronic anal fissures is a lateral internal sphincterotomy, which involves surgery to the internal anal sphincter. This procedure, however, requires hospitalisation and leads in a sizeable number of patients to impairment of continence (British Journal of Surgery 1996, 83, 1334-1344). As yet there is no proven non-surgical treatment for chronic fissure, although local injection of botulinum A toxin shows early promise (Martindale, The Extra Pharmacopoeia 31st Edition p 1516 and 1517).

A further potential non-surgical treatment that has recently been reported for anal fissures and haemorrhoids is the topical use of a nitric oxide donor, particularly glyceryl trinitrate. This reduces the internal anal resting pressure (British Journal of Surgery, 1994, 81, 1386-1389 and British Journal of Surgery, 1996, 83, 771-775 both by present inventors; Diseases of the Colon and Rectum, May 1995, p 453-457, The New England Journal of Medicine Oct. 26, 1995, p 1156 and 1157, WO 95/32715 and its equivalent U.S. Pat. No. 5,504,117—all by Gorfine; British Journal of Surgery 1996, 83, 776-777).

At a meeting of the Royal Society of Medicine Coloproctology Session on Nov. 27, 1996, a paper entitled "The effect of alpha adrenoceptor blockade on the anal canal in patients with chronic anal fissure" was presented showing that indoramin reduced maximum resting pressures in the anal canal after 1 hour by 35.8% in patients with anal fissures. The author suggested a clinical trial to determine the efficacy of indoramin in the treatment of anal fissures.

In Dis Colon Rectum, February 1996, vol 2, no. 2, p 212-216 nifedipine was reported as reducing the activity of the internal anal sphincter in patients with high anal resting pressure, and was proposed for use in relieving symptoms in patients with haemorrhoids or anal fissures.

Haemorrhoids ('piles') are venous swellings of the tissues around the anus. Those above the dentate line (the point where the modified skin of the outer anal canal becomes gut epithelium), which usually protrude into the anal canal, are termed internal haemorrhoids, while those below this point are called external haemorrhoids. Due to internal pressure, internal haemorrhoids tend to congest, bleed and eventually prolapse; with external haemorrhoids painful thrombosis may develop.

Initial treatment of internal haemorrhoids involves a high-fibre diet and avoidance of straining at stool, so bulk laxatives and faecal softeners may be indicated. Small bleeding haemorrhoids may be injected with a sclerosing agent such as oily phenol injection, or they may be ligated with rubber bands. More severe and prolonged prolapse generally requires surgery. Surgical excision to remove the clot is used for thrombosed external haemorrhoids.

A range of mainly topical drug treatments is available for symptomatic relief, but in many cases their value is a best unproven. Local anaesthetics may be included to relieve pain, and corticosteroids may be used when infection is not present. Preparations containing either group of drugs are intended only for short-term use. Some preparations include heparinoids and other agents frequently included for their soothing properties include various bismuth salts, zinc oxide, hamamelis, resorcinol and peru balsam.

In British Journal of Surgery 1994, 81, 946-954, Loder et al reviewed the possible pathology, pathophysiology and aetiology of haemorrhoids but came to no firm conclusions. The authors speculate that the anal cushions surround the anal canal act as a seal to prevent minor leakage from the anus and these cushions distend as a consequence of haemorrhoidal disease. The authors also explored whether haemorrhoids is more prevalent in certain racial groups, whether it is a function of diet, habits or body habitus, whether it is a genetic disorder or whether it is associated with other conditions such as hernia. No firm conclusions were, however, reached as to the aetiology of haemorrhoids or how to treat it effectively.

Diltiazem is indicated orally for the treatment of angina pectoris and hypertension, and may be given intravenously in the treatment of arterial fibrillation or flutter and paroxysmal supraventricular tachycardia. Bethanechol is used as an alternative to catheterisation in the treatment of urinary retention, gastric atony and retention, abdominal distension following surgery, congenital megacolon, and oesophageal reflux. It is given in doses of 5 mg subcutaneously or 10 to 50 mg by mouth (Martindale, The Extra Pharmacopoeia, 31st Edition, p 857 and p 1417).

In a letter to the Lancet Jun. 28, 1986 at p 1493 and Mar. 28, 1987 at p 754 diltiazem given orally at 60 mg was found to reduce internal anal resting pressure and to treat proctalgia fugax. There was, however, no suggestion of diltiazem being used to treat anal fissure or haemorrhoids.

SUMMARY OF THE INVENTION

It is an object of the present invention to provide a non-surgical treatment for anal fissures and/or haemorrhoids, or other benign anal disorders.

The inventors have now found that anal fissures and haemorrhoids and other benign anal disorders can be treated by local application to the anus of a cholinergic agent or a calcium channel blocker or a mixture thereof. Other benign anal disorders would be those conditions associated with a high anal pressure or where there is an associated anal sphincter spasm.

Accordingly in a first aspect of the invention, there is provided use of at least one of a cholinergic agent or a calcium channel blocker in the preparation of a medicament for local application to the anus for the treatment or prophylaxis of benign anal disorders.

To the inventors knowledge the active agents are usually administered orally or intravenously and have never before been contemplated in topical form. Accordingly, a second aspect of the invention provides a composition adapted for local application to the anus comprising at least one of a cholinergic agent or a calcium channel blocker together with a pharmaceutically acceptable carrier.

By local application to the anus we mean to include local injection into the anal sphincter, and administration in and around the anal canal, preferably by topical application such as spreading a topical composition in and around the anal canal.

Without being bound by theory, it is believed that the cholinergic agents and calcium channel blockers are at least partially effective (and there may be other mechanisms of action) by lowering the anal resting pressure of the patient. This helps the fissures to heal. This reduction in anal pressure should also allow better venous drainage which will allow the haemorroidal vascular cushions to heal.

In the case of haemorrhoids, it is also thought that the cholinergic agents will act to contract the longitudinal muscle of the anus, thereby pulling the haemorrhoidal cushions back into place.

In any case the clinical results to date suggest the inventors have made a major advance in the field by providing a safe and efficacious non-surgical treatment for anal fissures and haemorrhoids.

By anal fissures we mean to include both acute and chronic fissures or ulcers. Any patient with persistent symptoms for more than two weeks is taken to have a chronic fissure in accordance with the invention.

By haemorrhoids we mean to include both internal and external haemorrhoids and acute thrombosis of external haemorrhoid (TEM).

Suitable cholinergic agents in accordance with the invention are selected from a cholinergic agonist of acetylcholine, bethanechol, carbachol, methacholine, and pilocarpine, or an anticholinesterase of ambenonium, neostigmine, physostigmine, pyridostigmine, dyflos, and ecothinopate, and pharmaceutically acceptable salts of thereof.

Bethanechol and salts thereof is a particularly preferred cholinergic agent.

Suitable calcium channel blockers in accordance with the invention are selected from amlodipine, anipamil, barnidipine, benidipine, bepridil, darodipine, diltiazem, efonidipine, felodipine, isradipine, lacidipine, lercanidipine, lidoflazine, manidipine, mepirodipine, nicardipine, nifedipine, niludipine, nilvadipine, nimodipine, nisoldipine, nitrendipine, perhexiline, tiapamil, verapamil, and pharmaceutically acceptable salts thereof.

Diltiazem and salts thereof is a particularly preferred calcium channel blocker.

A further preferred aspect of the invention provides a composition for local application to the anus, particularly topically acting composition, but not exclusively for topical application in and around the anal canal comprising diltiazem or bethanechol or a combination thereof or pharmaceutically acceptable salts thereof, together with a pharmaceutically acceptable carrier.

Accordingly in a preferred aspect of the invention there is provided the use of diltiazem or bethanechol or a combination thereof and pharmaceutically acceptable salts thereof in the preparation of a topical medicament for the treatment or prophylaxis of benign anal disorders, particularly in the treatment of anal fissures and haemorrhoids.

Pharmaceutically acceptable salts of the aforementioned agents, such as of diltiazem and bethanechol, include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, benzenesulphonic, and isethionic acids. Salts of the compounds of formula (1) can be made by reacting the appropriate compound in the form of the free base with the appropriate acid. Salts of halides are also suitable. Diltiazem hydrochloride, diltiazem malate and diltiazem have CAS registry numbers respectively as follows: 33286-22-5, 144604-00-2, and 42399-41-7. Bethanechol and bethanechol chloride have CAS registry numbers respectively of 674-38-4 and 590-63-6.

Diltiazem and bethanechol are of great benefit when topically administered separately, but are of particular benefit and apparently exhibit a synergistic activity when administered together.

A suitable proportion of calcium channel blocker, such as diltiazem in a topical or local composition for a beneficial effect is at least 0.5% w/w, such as 0.5% to 10% w/w, preferably 0.5% to 5% w/w, more preferably still 1% to 5% w/w, still more preferably 1% to 3%, and most preferably about 2% w/w. Preliminary dose ranging studies suggest that the maximum effect of the invention is obtained at about 2% and thereafter higher concentrations will not produce a substantial additional effect.

The diltiazem composition is suitably applied 3 to 6 times, preferably 3 to 4 times daily, which based on 8 mg per application, gives a total daily dose of 24 mg to 48 mg.

A suitable proportion of cholinergic agent, such as bethanechol in a topical or local composition is at least 0.01% w/w, more preferably at least 0.05% such as 0.01% to 3% w/w, preferably 0.01% to 1% w/w, more preferably 0.05% to 1% w/w, and most preferably about 0.1% w/w. Preliminary dose ranging studies suggest that 0.1% w/w produced the maximum effect of the invention, and thereafter higher concentrations will not produce an additional effect.

The bethanechol composition is suitably applied in the same regimin as above which based on 0.4 mg per application, gives a total daily dose of 1.2 mg to 2.4 mg.

Pharmaceutical compositions adapted for topical administration in and/or around the anal canal may be formulated as ointments, creams, suspensions, lotions, powders, solutions, pastes, gels, sprays, foam, oils, aerosols, suppositories or enemas.

The topical compositions can comprise emulsifiers, preservatives, buffering agents and anti-oxidants. Preferably the compositions also comprise steroids (e.g. present at 0.1 to 5% w/w) such as prednisolone, busenonide or hydrocortisone, locally acting anaesthetics such as lignocaine (e.g. at 0.1 to 5% w/w), and soothants. Typical components used in existing fissure or haemorrhoidal treatments which can also be used in topical compositions of the invention include: zinc oxide, benzyl benzoate, bismuth oxide, bismuth subgallate and Peru balsam.

In accordance with the invention, the cholinergic agent or calcium channel blocker can be administered in combination with trinitroglycerine or any other nitric oxide donor, isoprenaline, histamine, prostaglandin E.sub.2, adenosine triphosphate, nictotine, DMPP, bradykinin, caerulein, glucagon, and phentolamine.

The topical composition may comprise skin penetrating agents, particularly the sulphoxides, such as dimethyl sulphoxide (DMSO) preferably at 25% to 50% w/w. Amides, (DMA, DMF) pyrrolidones, organic solvents, laurocaprom (AZONE) and calcium thioglycollate are suitable alternative penetrants. The composition may also optionally contains a polyacrylic acid derivative, more particularly a carbomer. This would both act as a skin hydrating agent to aid penetration of the drug, but also an emulsifying agent. The carbomer will help emulsify the DMSO, thereby mitigating skin irritation and providing enhanced skin hydration. Propylene glycol may also be present in the composition to soften the skin, increase thermodynamic potential and aid skin penetration by the DMSO and thus the drug. The final pH of the composition is advantageously pH 3.5 to 4.5.

Further aspects of the invention are as follows:

A. A method for the treatment or prophylaxis of a benign anal disorder comprising local application to the anus or the internal anal sphincter at least one of a cholinergic agent or calcium channel blocker.

B. An anal fissure and haemorrhoidal topical composition comprising at least one of a cholinergic agent or calcium channel blocker, together with a pharmaceutically acceptable carrier.

Early investigations suggest that the DMSO cream in the clinical studies may also have a therapeutic effect independent of the bethanechol or diltiazem. Thus a yet further aspect of the invention provides use of DMSO as a therapeutically active agent in the preparation of a topical medicament for the treatment of benign anal disorders, particularly anal fissure or haemorrhoids.

Preferably the DMSO is present at 25% to 50% w/w, and is advantageously present in combination with propylene glycol, preferably in a ratio by w/w of 5:1 to 15:1. The DMSO composition of this further aspect of the invention is also advantageously present with a polyacrylic acid derivative, such as carbomer, preferably at a ratio by w/w of 20:1 to 80:1. Preferably the pH of the composition is pH 3.5 to 4.5.

The invention will now be described by way of example only with reference to the accompanying drawings, in which:

DETAILED DESCRIPTION OF THE INVENTION

Example 1

Figure 1:
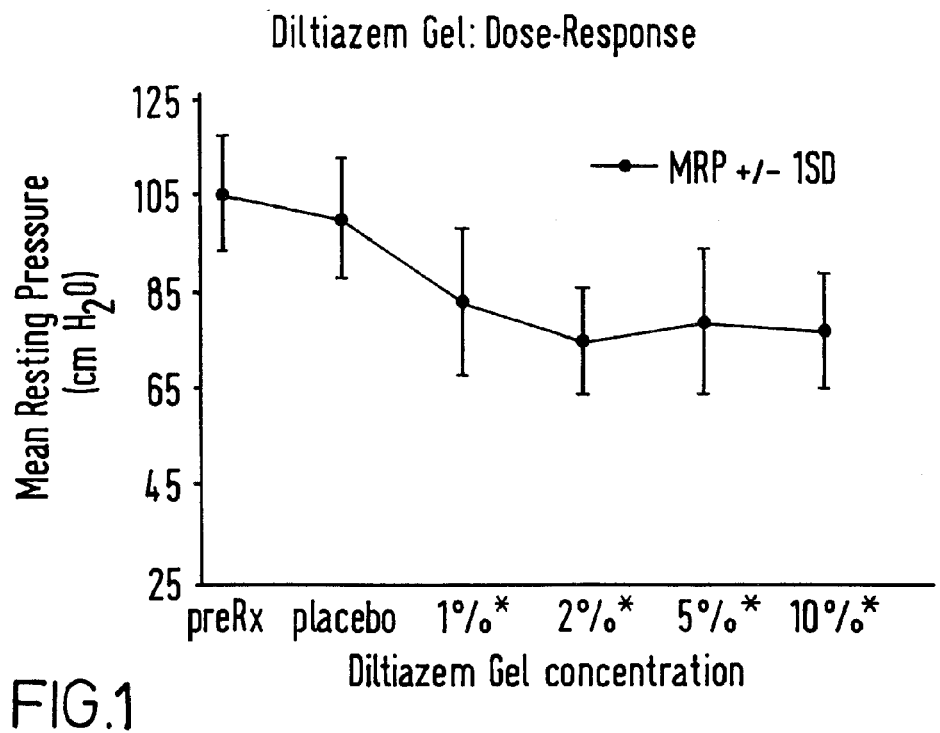
FIG. 1 is a graph of the dose response of diltiazem gel against mean anal resting pressure.

A composition of base gel had the following composition: carmellose sodium 6 g, polyethylene glycol 30 ml, methylhydroxybenzoate 150 mg, propylhydroxybenzoate 15 mg, made up to volume with distilled water (pH6-7).

Various amounts of diltiazem and bethanechol were added in the amounts shown in examples 4 and 6 to form various compositions for dose ranging studies.

Example 2

A base cream of the invention had the following composition:

| | |
|---|---|
| Diltiazem hydrochloride (2% w/w) | 10 g |
| Dimethyl sulphoxide | 250 g |
| Carbomer 974P | 5 g |
| White soft paraffin | 15 g |
| Cetomacrogel emulsifying ointment* | 115 g |
| Propylene glycol | 23 g |
| Methylhydroxybenzoate (preservative soln) to | 500 g |

*composition: white soft paraffin 50 g, liquid paraffin 20 g, cetomacrogol emulsifying wax 30 g (cetosteryl alcohol 24 g and cetomacrogol 1000, 6 g).

A base cream was formed by firstly separate mixing of the aqueous and non-aqueous components of the cream. Weighed quantities of propylene glycol and a proportion of the preservative solution were placed in a beaker to which the weight quantity of carbomer powder was added using an impeller type mixer to form a colloidal suspension of the carbomer. Thereafter, the weighed quantity of DMSO was added and rapid stirring continued at room temperature until a translucent uniform gel had been formed.

In the meantime, the weighed quantities of white soft paraffin and the cetamacrogol emulsifying ointment were placed in a separate beaker, heated to melting point and gently stirred to give a uniform base.

The drug is then added to the remainder of the preservative solution, which in turn was then added to the gel and whilst vigorously stirring, the uniform base (above) was added to form a cream. The carbomer acted as a dual neutralisation agent and primary emulsifier (of the oil and aqueous phases) to form the uniform cream base.

Example 3

A bethanechol cream composition was made up as above, but using 0.5 g of bethanechol (0.1% w/w) instead of diltiazem.

Example 4

Diltiazem Cream and Tablet—Dose Ranging Study on Healthy Volunteers

Figure 2:
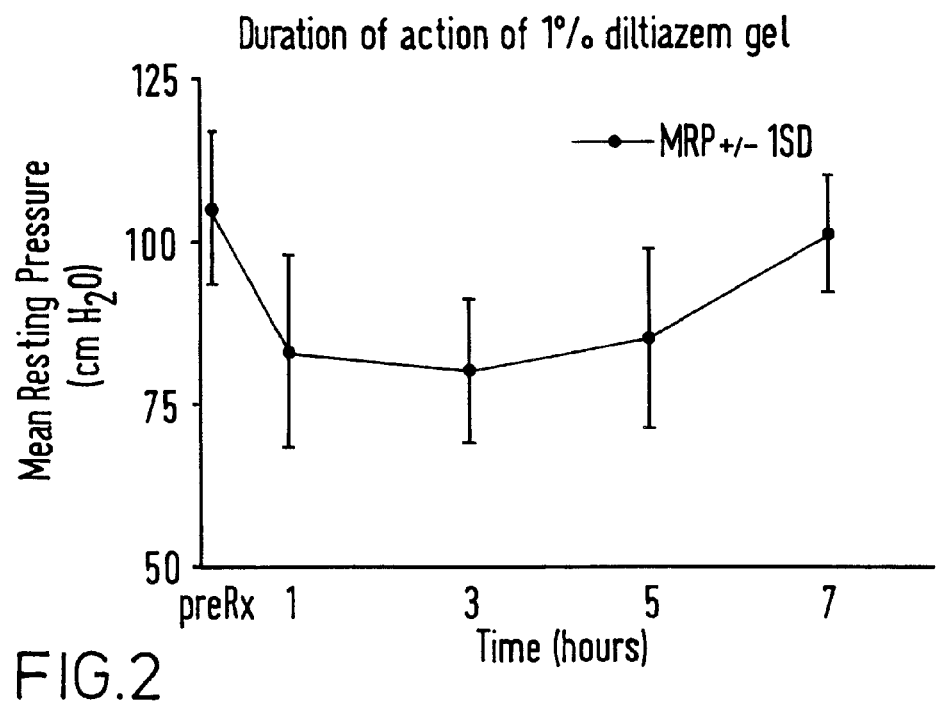
FIG. 2 is a graph of duration of action of 1% w/w diltiazem gel against mean anal resting pressure.

Ten volunteers were used in a double blind study to determine the concentration of diltiazem cream (of example 1) which most effectively lowers resting anal sphincter pressure as measured by an eight channel water perfused manometer. Concentrations of diltiazem cream used were 0.1%, 0.5%, 1%, 2%, 5% and 10%. Results showed a dose dependent reduction of the resting anal sphincter pressure. The maximal effect, at which the mean resting anal pressure was lowered by 28% (P<0.0001), was produced by 2% w/w cream (See FIG. 1). Higher concentrations did not produce an additional effect. A typical 'one inch' application of the cream from the tube is equivalent to 8 mg dose of diltiazem. Measurements taken throughout the day showed the effect of a single application to be sustained for 3 to 5 hours (see FIG. 2).

Example 5

Open Study of Diltiazem Cream in Patients with Anal Fissures

2% diltiazem cream from example 2 was applied to the anus three times daily for 8 weeks to treat patients suffering from chronic anal fissures (in an uncontrolled, open, pilot study). To date, 7 patients were studied and followed up between 2 to 5 weeks. 5 patients have had complete resolution of symptoms, of whom 3 have complete and 2 partial healing of the fissure. In four of these 5 patients there has been a reduction of the maximum resting anal sphincter pressure to within normal limits. The last patient, though symptom free, continues to have a high anal resting pressure.

2 patients have only had two weeks of treatment and one is symptom free after this short period, whilst the other still has occasional pain. It is too early to comment on healing of fissures in these two patients.

Example 6

Bethanechol Cream —Dose Ranging Study in Healthy Volunteers

Ten volunteers were used in a double blind study to determine the concentration of bethanechol gel which most effectively lowered resting anal sphincter pressure.

Figure 3:
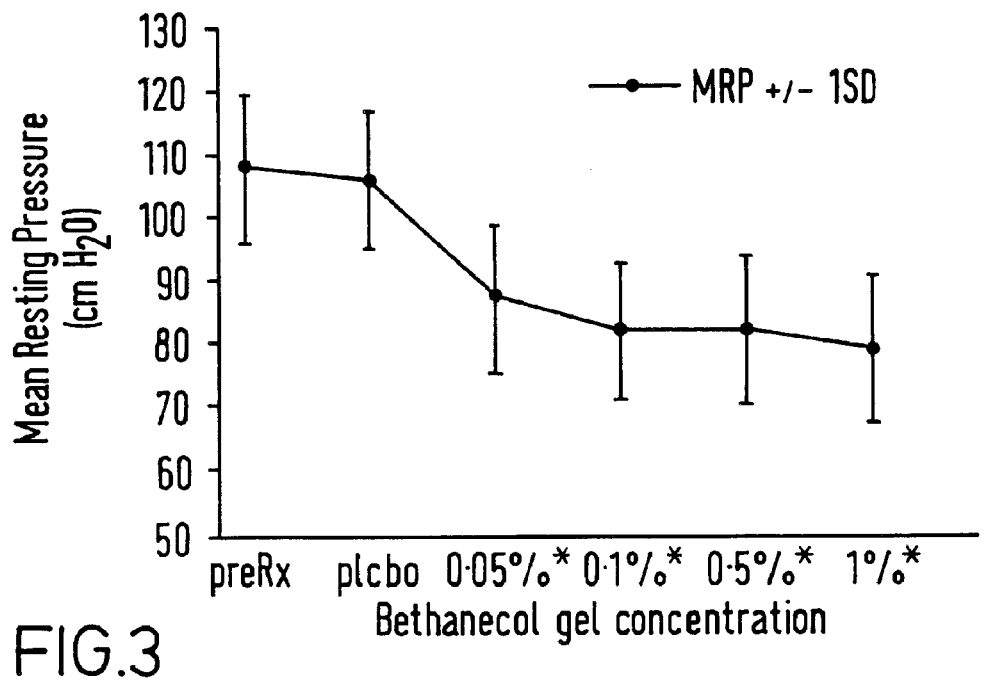
FIG. 3 is a graph of the dose response of bethanechol gel against mean anal resting pressure.
Figure 4:
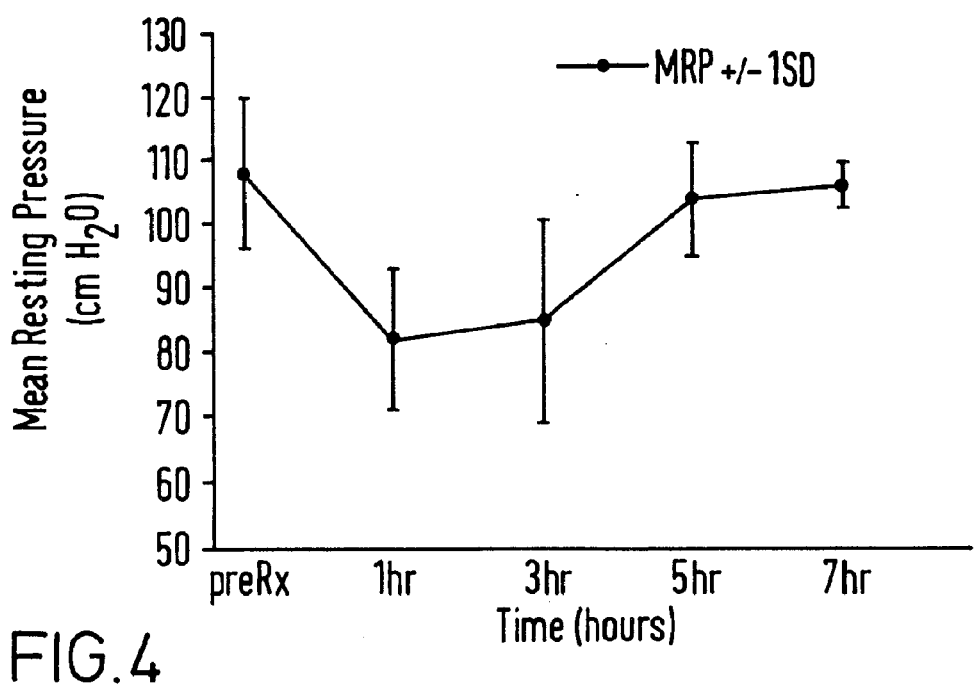
FIG. 4 is a graph of duration of action of 0.1% w/w bethanechol gel against mean anal resting anal pressure.

Bethanechol cream at concentrations of 0.05%, 0.1%, 0.5% and 1% w/w bethanechol were made up in accordance with example 1. The compositions were studied following initial experimentation in an open way to determine a clinically effective dose range. Results showed a dose dependent reduction in the resting anal sphincter pressure (see FIG. 3). Maximal effect was produced by application of 0.1% bethanechol and higher concentrations of the cream produced no additional effect. At 0.1% w/w bethanechol, the mean resting pressure was reduced from about 110 cm to about 85 cm H.sub.2O (about 25% decrease). A typical 'one inch' application of this cream from the tube is equivalent to 400 mcg of bethanechol. Measurements taken throughout the day showed the effect of a single application to be sustained from 3 to 5 hours (see FIG. 4).

Example 7

Open Study of Bethanechol Cream in Patients with Chronic Anal Fissures

The 0.1% bethanechol cream of example 3 was applied to the anus three times daily for an eight week course to treat patients suffering from chronic anal fissures (in an uncontrolled, open, pilot study). To date, 6 patients have been treated and followed up for 3 to 5 weeks. Four patients have had complete resolution of symptoms, of whom 3 have complete and 1 partial healing of the fissure. In all of these 4 patients there has been a reduction of the maximum resting anal sphincter pressure to within normal limits. One patient discovered she was pregnant and treatment was discontinued. The last patient has had no relief and remains symptomatic after 4 weeks' follow up.

These results shows that both bethanechol and diltiazem (applied topically) reduce the resting anal sphincter pressure in healthy and diseased patients. The preliminary open studies, albeit in a small group of patients, has shown a significant healing rate and symptom relief after only a few weeks application of both agents. This is a major achievement for the non-surgical treatment of fissures and offers hope to its many sufferers.

When the study of example 4 was repeated using 60 mg oral diltiazem once a day, no notable effect was obtained. At 60 mg twice a day, the mean anal resting pressure was reduced by 17% (P=0.008), but two patients notices postural dizziness. Topical diltiazem is surprisingly safer and more effective than oral diltiazem.

Example 8

In a combined bethanechol and diltiazem study, six healthy volunteers had topically applied to their anus on different days:
1) diltiazem at 2% w/w alone;
2) bethanechol at 0.1% w/w alone; and
3) diltiazem and bethanechol combined.

Figure 5:
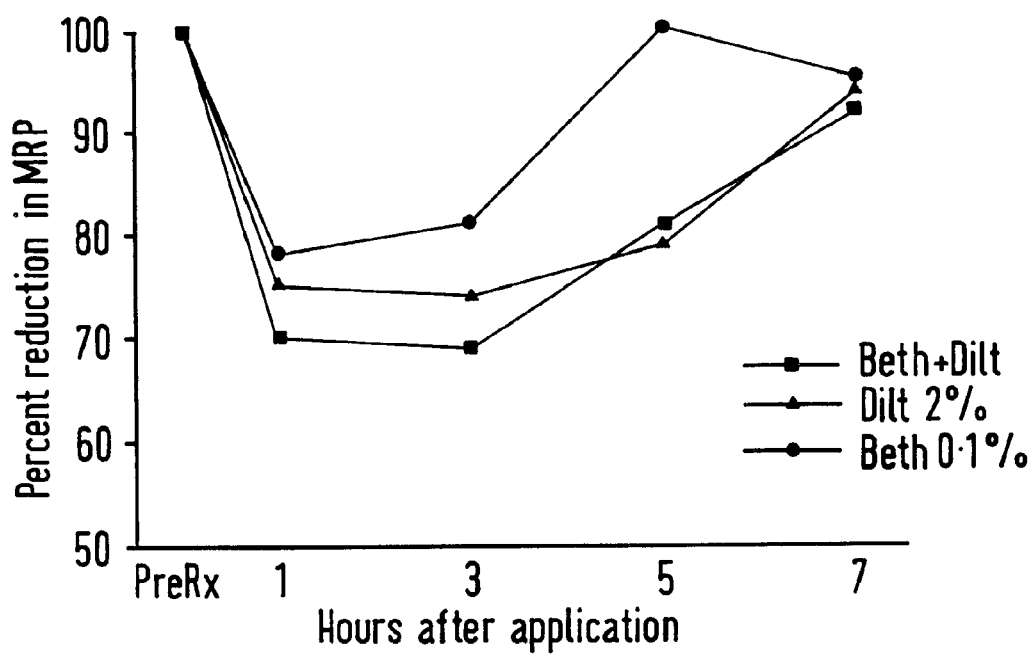
FIG. 5 is a graph comparing 2% diltiazem, 0.1% bethanechol, and a combination of both over time against the reduction in mean anal resting pressure.

Anal mamometry was carried out before and after each of the three creams were applied and repeated at two hourly intervals. The mean results are shown in FIG. 5.

These show that the combination of diltiazem and bethanechol gives a larger reduction in the mean anal resting pressure than either of diltiazem or bethanechol alone. This synergy may be due to both agents working in different mechanistic pathways to effect the pressure drop.

In summary, the results show that local application to the anus of at least one of a cholinergic agent or calcium channel provides a efficacious treatment for benign anal disorder, particularly anal fissures and haemorrhoids. Furthermore since efficacy can be obtained at surprisingly low doses, the treatment of the invention is also substantially free of side effects normally associated with the active agents.

That which is claimed is:

1. A method for the treatment of benign anal disorders associated with high anal pressure or anal sphincter spasm selected from the group consisting of anal fissures and hemorrhoids, the method comprising:
spreading in and around the anal canal of a patient a topical composition, wherein the topical composition consists of:
a sole active component that treats anal fissures and hemorrhoids consisting of 2% w/w of a compound selected from diltiazem and a pharmaceutically acceptable salt of diltiazem; and at least one non-active component selected from the group consisting of emulsifiers, preservatives, buffering agents, paraffin and organic solvents, wherein the topical composition is spread in and around the anal canal of the patient in a one inch dosage containing 8 mg of diltiazem.

2. The method according to claim 1, wherein the topical composition is applied three times daily.

* * * * *